United States Patent [19]
Ravdin et al.

[11] Patent Number: 5,862,304
[45] Date of Patent: *Jan. 19, 1999

[54] METHOD FOR PREDICTING THE FUTURE OCCURRENCE OF CLINICALLY OCCULT OR NON-EXISTENT MEDICAL CONDITIONS

[75] Inventors: Peter M. Ravdin; William L. McGuire; Gary M. Clark, all of San Antonio, Tex.

[73] Assignee: Board of Regents, The University of Texas System, Austin, Tex.

[*] Notice: The terminal 21 months of this patent has been disclaimed.

[21] Appl. No.: 607,120

[22] Filed: Oct. 31, 1990

Related U.S. Application Data

[63] Continuation-in-part of Ser. No. 526,224, May 21, 1990, abandoned.

[51] Int. Cl.$^6$ ............................................. G06F 15/18
[52] U.S. Cl. ................................... 395/22; 364/413.01
[58] Field of Search ........................... 364/413.1, 513; 395/22

[56] References Cited

U.S. PATENT DOCUMENTS

| | | | |
|---|---|---|---|
| 3,909,792 | 9/1975 | Harris et al. | 340/172.5 |
| 3,921,147 | 11/1975 | Fuhr et al. | 340/172.5 |
| 4,041,468 | 8/1977 | Perry et al. | 364/900 |
| 4,290,114 | 9/1981 | Sinay | 364/900 |
| 4,965,725 | 10/1990 | Rutenberg | 364/413.1 |

OTHER PUBLICATIONS

Saito et al., "Medical Diagnostic Expert System Based on PDP Model," IEEE Intl. Conf. on Neural Networks, Jul. 1988, I 255–262.

Bounds et al., "A Multi Layer Perceptron Network for the Diagnosis of Low Back Pain", IEEE Intl Conf. on Neural Networks, Jul. 1988, II, 481–489.

McClelland et al., Explorations in Parallel Distributed Processing, MIT Press, 1988, 2, 3, 121–145.

Bailey et al., "The Practical Side of Neural Networks–Part Two", PCAI, Mar./Apr. 1989, 56–58.

Canu et al., "Formal Neural Network as an Adaptive Model for Water Demand", Intl. Neural Networks Conf., Jul. 1990, 131–136.

Wilcox et al., "Protein Tertiary Structure Prediction Using A Large Backpropagation Network", Intl. Neural Networks Conf., Jul. 1990, 365–369.

Bounds et al., "A Comparison of Neural Network and Other Pattern Recognition Approaches to the Diagnosis of Low Back Disorders", Neural Networks, vol. 3, No. 5, 1990, 583–591.

Frankel et al., "Use of a Neural Net Computer System for Analysis of Flow Cytometric Data of Phytoplankton Populations", IJCNN, Jun. 1989, II 575.

Dixon et al., Introduction to Statistical Analysis, McGraw–Hill, Inc., 1969, pp. 5–11, 37–52.

Kane et al., "AI in Medicine", AI Expert, Nov. 1988, pp. 48–55.

McClelland et al., Explorations in Parallel Distributed Processing, MIT Press, 1988, pp. 2–3, 137–145.

(List continued on next page.)

*Primary Examiner*—Robert W. Downs
*Attorney, Agent, or Firm*—Arnold, White & Durkee

[57] ABSTRACT

A method is presented for evaluating data to predict the future occurrence of a medical condition that is presently clinically occult or which has not yet occurred. Specifically, the method uses a neural network to analyze and interpret DNA flow cytometric histograms. A first set of DNA histograms taken from tumors from patients having known relapse rates are used to train the neural network, an then the trained network is applied to predict the relapse rates of patients using DNA histograms of tumors from those patients. Prognosis according to this method can be performed using only diploid histograms, using only aneuploid histograms, or using a combination of diploid and aneuploid histograms.

13 Claims, 9 Drawing Sheets

OTHER PUBLICATIONS

White, H., "Learning in Artificial Neural Networks: A Statistical Perspective", Neural Computation, 1, 1989, pp. 425–464.

Stephen I. Gallant, "Connectionist Expert Systems," *Communications of the ACM,* vol. 31, No. 2, pp. 152–169 (Feb. 1988).

Stubbs: 'Three applications of neurocomputing in biomedical research', IJCNN International Joint Conference on Neural Networks, vol. II, 1989, New York, p. 609.

Blumenfeld: 'A Connectionist Approach to the Recognition of Trends in Time Ordered Medical Parameters', Proceedings of the 13–th Annual Symposium on Computer Applications in Medical Care, 1989, pp. 288–294.

METHOD FOR PREDICTING THE FUTURE OCCURRENCE OF CLINICALLY OCCULT OR NON-EXISTENT MEDICAL CONDITIONS

This is a continuation-in-part application of Ser. No. 07/526,224, filed May 21, 1990, now abandoned.

BACKGROUND OF THE INVENTION

The present invention relates to a method for predicting the future occurrence of medical conditions that have not yet occurred or which are clinically occult.

Neural networks are well known and have been used to implement computational methods that learn to distinguish between objects or classes of events. The networks are first trained by presentation of known data about objects or classes of events, and then are applied to distinguish between unknown objects or classes of events. While neural networks have been applied in medicine to diagnose diseases based on existing symptoms, and to prescribe treatments for the diagnosed diseases, to date, there has been no application of such networks to predict future occurrence of disease which is clinically occult or which has not yet occurred, or to predict the relapse of disease that has presumably been cured.

Such prognostication is important in all branches of medicine. For example, it is useful in the field of oncology in order to improve the prediction of prognosis of patients so that appropriate therapy can be selected. This goal is of particular importance in the selection of treatment of breast cancer patients who are presumably rendered disease free after the removal of the primary tumor within the breast, and who have no pathological evidence of axillary lymph node involvement. Most of these patients will have been surgically cured, but a substantial minority will relapse.

Several recent studies suggest that certain breast cancer patients without axillary lymph node involvement can benefit by adjuvant chemotherapy or hormonal therapy. However, not all the individual patients actually benefit from this therapy, and a majority of these patients receive therapy that is not necessary.

Prior efforts to predict breast cancer prognosis use a number of biochemical, molecular biologic and biophysical input variables that can be used to describe the cells in a tumor. When such multiple input variables are available, typically various combinations of the input variables are assessed using multivariate analysis. Multivariate analysis is a powerful tool but suffers from the disadvantage that it is often unable to effectively analyze outcome based on a highly non-linear input variable. In addition it is at particular disadvantage in analyzing interactions between several non-linear variables (where for example multiple peaks and troughs of recurrence probability may exist). All of this is particularly true when a given input variable is included in one of two input states (as is commonly done in clinical medicine), with an optimum threshold or cut-point between the two states being determined by maximizing a likelihood function using regression analysis. While such multivariate analysis is not without advantage, it suffers from drawbacks because defining a single cut-point between two states of an input variable effectively ignores important non-linearities in the input variable. In addition, multivariate analysis can miss cross-correlation effects between input variables.

Other clinically occult diseases which have known multiple risk factors, for example, coronary heart disease or diabetes, would also benefit from improved prognostication methods.

Other methods have also proven to be important tools in the prediction of prognosis in breast cancer, and other tumor types. Such methods, known as DNA cytophotometry, process images of cells or cell components to quantitatively estimate a number of nuclear and cellular parameters. Of particular interest is DNA flow cytometry. The basis of DNA flow cytometry is the measurement of the level of DNA in individual cells. The technique results in DNA histograms indicating the number of cells having different levels of DNA. Conventionally, DNA histograms obtained through flow cytometry are interpreted as having cells in three basic regions: cells in the G1/G0 phase of the cell cycle before replication of DNA; cells in the S-phase which are actively replicating DNA; and cells in the G2/M phase of the cell after DNA replication but before cell replication.

Tumor cells are conventionally interpreted as diploid if they have a G0/G1 peak with a DNA content that is that of normal cells, if there are no other peaks in the histogram with an arbitrary cut-off percentage of counts (usually 10%) of that peak value, and if the G0/G1 peak in the histogram is narrow enough to be considered to represent cells of one population. S-phase counts of a DNA histogram lie in that region between the G0/G1 peak and the G2/M peak.

Several complex mathematical formulae have been developed to count the number of S-phase events while subtracting out events due to the tails of the G0/G1 and G2/M peaks, and while subtracting out the effects of contaminating cell debris. A particular sophisticated method known as SFIT uses second degree polynomials to perform this subtraction. These mathematical formulae are particularly complex for aneuploid histograms when they often have to deal with cell kinetics from cell populations that are both diploid and aneuploid. All of these mathematical approaches are however based on a mechanistic view of cells being in either the G0/G1, S or G2/M phases of the cell cycle.

As such, present techniques for analyzing DNA histograms resulting from flow cytometry ignore other patterns occurring in the DNA histograms which correlate with the risk of cancer relapse.

SUMMARY OF THE INVENTION

The present invention avoids the drawbacks of the prior art by presenting a medical prognostication method employing a neural network which is trained using sets of data including prognostic variables and corresponding disease or medical condition occurrence. After training, sets of test data, including the same prognostic variables with unknown disease occurrence, are tested to predict the future occurrence of the disease or medical condition.

According to the present invention, a neural network of the back-propagation class is trained using the back-propagation of errors training algorithm with data of patients with known prognostic variables and disease occurrence. After training, the method then uses the trained neural network to predict future disease occurrence using sets of prognostic variables for which disease occurrence is not known.

In two exemplary embodiments of the invention, a neural network is used to implement a method to analyze the outcome of breast cancer patients who have been apparently cured, but who are at risk for relapse. In another exemplary embodiment, a neural network is used to implement a method to analyze the risk of developing diabetes mellitus.

Specifically, in a first embodiment when predicting the relapse of cancer in breast cancer patients, the present invention uses as prognostic variables progesterone receptor values, tumor size, cathepsin D protein levels and HER-2/neu protein levels. These prognostic variables are quantized into discrete variables and applied to input units of a three-level neural network having two output units, one representing relapse and one representing non-relapse.

In a second embodiment of the invention, when analyzing the risk of developing diabetes mellitus, the present invention uses as prognostic variables age, fasting glucose level, two-hour glucose level, fasting insulin level, and body mass index.

In accordance with yet another embodiment of the present invention, a neural network is used to implement a method to analyze the risk of relapse of axillary node positive breast cancer patients based on histograms of DNA flow cytometric analysis of primary tumors. This method can be used to replace, or in conjunction with, convention DNA flow cytometric analysis.

Application of the present invention to predict the occurrence or relapse of other diseases, or to predict the mortality rate of diseases and other medical conditions (such as for an actuarial analysis) is also possible. For example, the present invention can be used as a tool in the prognosis of diseases and medical conditions such as other forms of cancer, cardiovascular disease, post-operative complications for various operative procedures, anesthesia related complications for various anesthetics, obstetrical complications, psychiatric problems, and other health related events.

DETAILED DESCRIPTION OF THE PREFERRED EMBODIMENTS

Figure 1:
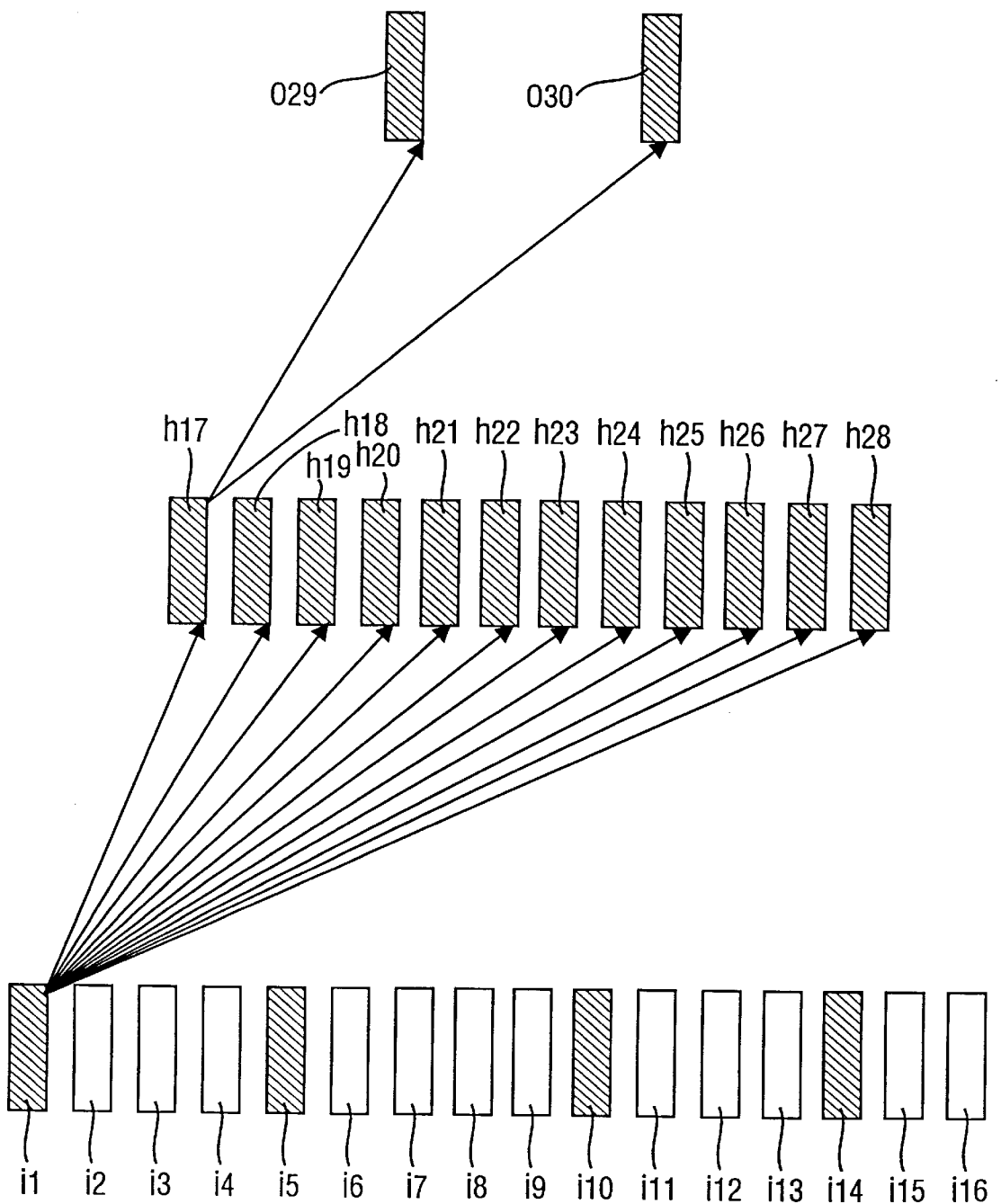
FIG. 1 is a schematic representation of a neural network used to practice the method of the present invention to predict relapse of breast cancer.

Referring to FIG. 1, presented is a schematic representation of a neural network used to practice the method of the present invention to predict the relapse rate of breast cancer patients. In this embodiment, a three-layer feed-forward neural network is used of the back-propagation class, and is trained using the back propagation of errors algorithm, both of which are known in the art. The network was simulated on a MacIntosh IIx computer using MacBrain 2.0 software developed by Neuronics, Inc. of Cambridge, Mass.

It should be emphasized that other forms of neural networks, for example adaline networks, adaptive resonance theory networks, bi-directional associative memory networks, back propagation networks, Boltzman back propagation networks, counter propagation networks, Hamming networks, Hopfield networks, Madaline networks, probablilstic neural networks, recirculation networks, spatio-temporal pattern recognition networks, and others, can be used for this and other embodiments without departing from the spirit and scope of the present invention.

In addition, different training algorithms, such as for example, the pocket algorithm, delta rule, counter propagation, Hebb rule, Hopfield rule, Windrow-Hoff rule, adaline rule, Kohonene rule, and similar neural network training algorithms, can also be used without departing from the spirit and scope of the present invention.

In FIG. 1, the neural network includes three layers, an input layer having sixteen units, i1–i16, a hidden layer having twelve units, h17–h28, and an output layer including two output units, o29 and o30. For clarity of presentation, only the connections between one of the input units, i1, and the hidden layer units are shown, and only the connections between one of the hidden units, h17, and the output layer units are shown. In actuality, each of the input units i1–16 is connected to each of the hidden layer units h17–h28, and each of the hidden layer units h17–h28 is connected to each of the output units o29 and o30. Thus, there are a total of 192 connections between the input and hidden layer units, and a total of 28 connections between the hidden layer and output layer units.

After training (described in more detail below), the connections between the various units of the neural network are weighted, and the output, or "activation state" of one unit is multiplied by the weight of the connection before application as an input to a unit in the next layer.

The activation state of each input unit i1–i16 is simply determined by the input of a one or a zero value depending on whether the relevant prognostic variable of a particular patient was positive or not. The inputs of each input unit i1–i16 are all applied at the same time, and are used to determine the activation states of the hidden layer units, h17–h28. The activation state of each hidden layer unit is calculated according to the sigmoidal activation equation:

$$\text{Activation State} = 1/(1+e^{-Wi/x})$$

Where: Wi is the sum of all weighted inputs to the unit (i.e., the sum of the activation states of the inputs to the unit, each multiplied by the relevant connection weight), and where x is equal to 0.2. The values for the activation states of each unit calculated using this activation equation are values between zero and one. The activation states of all hidden layer units, h17–h28, are calculated at the same time.

The hidden layer activation states are then used to calculate the activation states of output units, o29 and o30, using the same activation equation used to calculate the states of the hidden layer units. For each output unit, the contribution of each hidden layer unit to each output unit is calculated by multiplying the activation state of each hidden layer unit by the connection weight between it and the relevant output unit.

The activation states of output units o29 and o30, one representing relapse and the other representing non-relapse, are then used to predict prognosis based on the input data. Non-relapse is defined as the output unit representing non-relapse having an activation state greater than 0.5 and the output unit representing relapse having an activation state less than 0.5. Relapse is defined as all other states. Alternatively, in a known manner, during training, the activation states of output units o29 and o30 are compared with known relapse data and are used to train the neural network.

Input units, i1–i16, are divided into groups according to a particular prognostic input variable, and each input unit is dedicated to a particular range for the corresponding input variable. In this exemplary embodiment, the input prognostic variables used to predict the occurrence of relapse in breast cancer are: progesterone receptor values (PgR) measured in femtomoles per milligram; tumor size, measured in centimeters; cathepsin D protein level, measured in expression units; and HER-2/neu protein level, also measured in expression units. Units i1–i4 are used for coding progesterone receptor values, units i5–i7 for tumor size, units i8–i11 for cathepsin D levels, and units i12–i16 for HER-2/neu protein levels. These four prognostic variables are quantized into discrete values, with each input unit representing approximately 1/N of the patients within the training data set, where N equals the number of input units used to input the information for a particular prognostic variable. Table I shows the actual cut-off values used for each prognostic input variable.

TABLE I

PARTITIONING OF PROGNOSTIC VARIABLES
FOR RELAPSE OF BREAST CANCER
Break Points For Input Units

| Input Unit | Variable | Range |
|---|---|---|
| i1 | PgR | <3 (fm/mg) |
| i2 | " | ≧3 and <10 |
| i3 | " | ≧10 and <60 |
| i4 | " | ≧60 |
| i5 | Tumor Size | <3 (cm) |
| i6 | " | ≧3 and <4 |
| i7 | " | ≧4 |
| i8 | Cathepsin D | <10 (E.U.) |
| i9 | " | ≧10 and <30 |
| i10 | " | ≧30 and <100 |
| i11 | " | ≧100 |
| i12 | HER-2/neu | <3 (E.U.) |
| i13 | " | ≧3 and <10 |
| i14 | " | ≧10 and <30 |
| i15 | " | ≧30 and <100 |
| i16 | " | ≧100 |

To demonstrate the present invention, a data set including 199 breast cancer patients having no evidence of axillary lymph node involvement was used. The information for each patient included values for the prognostic variables, as well as follow-up information including relapse occurrence and mortality.

Patients were randomly assigned either to a training set of 133 patients, which were used to teach the neural network, or a test set of 66 patients that were used to test the ability of the invention to generize from the training set to patients that the network had not previously processed. For teaching, connection weights between the units were initially randomly assigned to values between negative one and one, and using the known back propagation of errors algorithm for training, the entire training set of 133 was applied to the neural network for several iterations, during which the individual connection weights are adjusted.

Table II presents the connection weights between all of the units of FIG. 1 after 35 training iterations of the training set.

TABLE II

NEURAL NETWORK CONNECTION WEIGHTS
FOR BREAST CANCER PROGNOSIS

| TO UNIT NO. | WEIGHT |
|---|---|
| WEIGHTS TO OTHER UNITS FROM UNIT NO. i1 | |
| h17 | -.3906 |
| h18 | -.4709 |
| h19 | .2956 |
| h20 | -.7570 |
| h21 | -.7437 |
| h22 | .4515 |
| h23 | -.6557 |
| h24 | -.6805 |
| h25 | -.0680 |
| h26 | -.6790 |
| h27 | -.1473 |
| h28 | .4582 |
| WEIGHTS TO OTHER UNITS FROM UNIT NO. i2 | |
| h17 | .5320 |
| h18 | .1984 |
| h19 | .1884 |
| h20 | -.9822 |
| h21 | .0284 |
| h22 | -.7155 |
| h23 | .4733 |
| h24 | -.4532 |
| h25 | 0.0 |
| h26 | -.3023 |
| h27 | -.0666 |
| h28 | .4905 |
| WEIGHTS TO OTHER UNITS FROM UNIT NO. i3 | |
| h17 | .2177 |
| h18 | .3684 |
| h19 | -.6216 |
| h20 | .3037 |
| h21 | .6173 |
| h22 | -.5931 |
| h23 | .3495 |
| h24 | .5605 |
| h25 | .4034 |
| h26 | .9060 |
| h27 | -.4727 |
| h28 | -.2158 |
| WEIGHTS TO OTHER UNITS FROM UNIT NO. i4 | |
| h17 | -.9462 |
| h18 | .2226 |
| h19 | -.2883 |
| h20 | -.6021 |
| h21 | -.7095 |
| h22 | 1.0270 |
| h23 | -.3167 |
| h24 | -.1635 |
| h25 | -.6571 |
| h26 | .8319 |
| h27 | .8953 |
| h28 | -.5648 |
| WEIGHTS TO OTHER UNITS FROM UNIT NO. i5 | |
| h17 | .1531 |
| h18 | .1268 |
| h19 | -.7091 |
| h20 | .3348 |
| h21 | .6779 |
| h22 | .4736 |
| h23 | -.9540 |
| h24 | .4526 |
| h25 | .2061 |
| h26 | .4309 |
| h27 | -.4772 |
| h28 | .0857 |
| WEIGHTS TO OTHER UNITS FROM UNIT NO. i6 | |
| h17 | .2223 |
| h18 | -.8737 |

TABLE II-continued

NEURAL NETWORK CONNECTION WEIGHTS FOR BREAST CANCER PROGNOSIS

| TO UNIT NO. | WEIGHT |
|---|---|
| h19 | −.3644 |
| h20 | −.7821 |
| h21 | .6008 |
| h22 | −.4216 |
| h23 | .7886 |
| h24 | −1.0390 |
| h25 | .1462 |
| h26 | .3355 |
| h27 | .6250 |
| h28 | .3332 |

WEIGHTS TO OTHER UNITS FROM UNIT NO. i7

| h17 | .2973 |
| h18 | .5655 |
| h19 | −.0527 |
| h20 | −.5303 |
| h21 | .3262 |
| h22 | .3978 |
| h23 | .2357 |
| h24 | .2703 |
| h25 | −.0321 |
| h26 | .1099 |
| h27 | −.5590 |
| h28 | −.9910 |

WEIGHTS TO OTHER UNITS FROM UNIT NO. i8

| h17 | −.4898 |
| h18 | .1949 |
| h19 | .7300 |
| h20 | .4900 |
| h21 | .4681 |
| h22 | −.2509 |
| h23 | .8567 |
| h24 | .7537 |
| h25 | −.9103 |
| h26 | −.8041 |
| h27 | −.7081 |
| h28 | .2244 |

WEIGHTS TO OTHER UNITS FROM UNIT NO. i9

| h17 | −.2187 |
| h18 | .7734 |
| h19 | 1.1569 |
| h20 | .0239 |
| h21 | .002394 |
| h22 | −.6399 |
| h23 | .0663 |
| h24 | −.5284 |
| h25 | −.9612 |
| h26 | −.04007 |
| h27 | .5389 |
| h28 | .8457 |

WEIGHTS TO OTHER UNITS FROM UNIT NO. i10

| h17 | −.8341 |
| h18 | .0639 |
| h19 | −.6858 |
| h20 | −.2301 |
| h21 | −.7466 |
| h22 | −.3080 |
| h23 | .1498 |
| h24 | −.8082 |
| h25 | −.9401 |
| h26 | 1.0440 |
| h27 | .3064 |
| h28 | −.6399 |

WEIGHTS TO OTHER UNITS FROM UNIT NO. i11

| h17 | .8557 |
| h18 | −.0135 |
| h19 | .6326 |
| h20 | .8184 |
| h21 | −.5939 |
| h22 | .6688 |

TABLE II-continued

NEURAL NETWORK CONNECTION WEIGHTS FOR BREAST CANCER PROGNOSIS

| TO UNIT NO. | WEIGHT |
|---|---|
| h23 | .2576 |
| h24 | .3858 |
| h25 | −.6883 |
| h26 | .7371 |
| h27 | .0915 |
| h28 | .0777 |

WEIGHTS TO OTHER UNITS FROM UNIT NO. i12

| h17 | .2551 |
| h18 | −.7630 |
| h19 | .4250 |
| h20 | −.6815 |
| h21 | −.6349 |
| h22 | −.7121 |
| h23 | −.5656 |
| h24 | −.9477 |
| h25 | −.6794 |
| h26 | .8768 |
| h27 | −.2034 |
| h28 | −.8815 |

WEIGHTS TO OTHER UNITS FROM UNIT NO. i13

| h17 | −.4228 |
| h18 | .3897 |
| h19 | −.0624 |
| h20 | −.1254 |
| h21 | −.3533 |
| h22 | .2385 |
| h23 | .3233 |
| h24 | −.0850 |
| h25 | −.1422 |
| h26 | −.2288 |
| h27 | −.0247 |
| h28 | −.2515 |

WEIGHTS TO OTHER UNITS FROM UNIT NO. i14

| h17 | −.0540 |
| h18 | −.6162 |
| h19 | −.0116 |
| h20 | −.5482 |
| h21 | .7184 |
| h22 | −.6320 |
| h23 | −.1000 |
| h24 | .9118 |
| h25 | .4984 |
| h26 | −.1832 |
| h27 | −.00292 |
| h28 | −.4219 |

WEIGHTS TO OTHER UNITS FROM UNIT NO. i15

| h17 | .7094 |
| h18 | −.3693 |
| h19 | −.6769 |
| h20 | .02239 |
| h21 | −.5683 |
| h22 | −.0709 |
| h23 | −.7757 |
| h24 | .8521 |
| h25 | −.1306 |
| h26 | −.1435 |
| h27 | .4659 |
| h28 | .0634 |

WEIGHTS TO OTHER UNITS FROM UNIT NO. i16

| h17 | −.2348 |
| h18 | −.1824 |
| h19 | .00003935 |
| h20 | −.7847 |
| h21 | .2633 |
| h22 | −.6176 |
| h23 | .3287 |
| h24 | .07218 |
| h25 | .4740 |
| h26 | −.6646 |

TABLE II-continued

NEURAL NETWORK CONNECTION WEIGHTS
FOR BREAST CANCER PROGNOSIS

| TO UNIT NO. | WEIGHT |
|---|---|
| h27 | -.5862 |
| h28 | .2196 |
| WEIGHTS TO OTHER UNITS FROM UNIT NO. h17 | |
| o29 | .2265 |
| o30 | -.04278 |
| WEIGHTS TO OTHER UNITS FROM UNIT NO. h18 | |
| o29 | -.08828 |
| o30 | .3799 |
| WEIGHTS TO OTHER UNITS FROM UNIT NO. h19 | |
| o29 | .1962 |
| o30 | .6201 |
| WEIGHTS TO OTHER UNITS FROM UNIT NO. h20 | |
| o29 | -.2701. |
| o30 | .07405 |
| WEIGHTS TO OTHER UNITS FROM UNIT NO. h21 | |
| o29 | -.8166 |
| o30 | .1395 |
| WEIGHTS TO OTHER UNITS FROM UNIT NO. h22 | |
| o29 | .2786 |
| o30 | -.3387 |
| WEIGHTS TO OTHER UNITS FROM UNIT NO. h23 | |
| o29 | .7487 |
| o30 | -.3231 |
| WEIGHTS TO OTHER UNITS FROM UNIT NO. h24 | |
| o29 | -.5020 |
| o30 | .4133 |
| WEIGHTS TO OTHER UNITS FROM UNIT NO. h25 | |
| o29 | .7717 |
| o30 | -.1384 |
| WEIGHTS TO OTHER UNITS FROM UNIT NO. h26 | |
| o29 | .5795 |
| o30 | .3488 |
| WEIGHTS TO OTHER UNITS FROM UNIT NO. h27 | |
| o29 | -.5913 |
| o30 | .6090 |
| WEIGHTS TO OTHER UNITS FROM UNIT NO. h28 | |
| o29 | -.2601 |
| o30 | 1.0440 |

Figure 2:
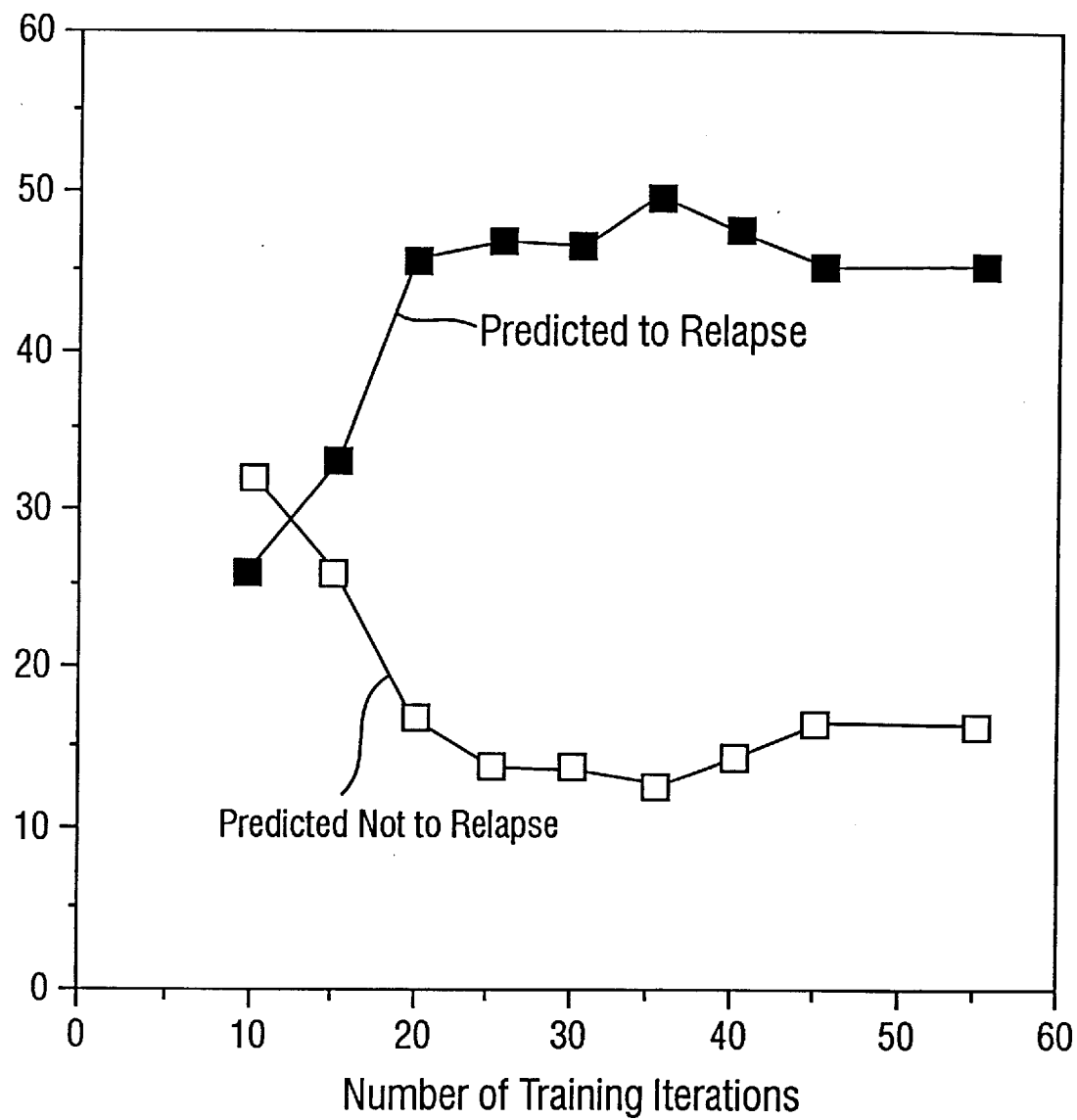
FIG. 2 is a graph of the performance of the present invention in predicting relapse of breast cancer plotted against the number of training iterations.

FIG. 2 is a graph illustrating the learning process through successive learning iterations in order to make successful predictions of patient relapse in the set of 66 patients in the testing set. As can be seen in FIG. 2, the network is at first essentially making random guesses. After 20 learning iterations, the network is making predictions that are significantly better than chance with p less than 0.012. After 35 training iterations through the entire training set, the network was correct in 50% of its prediction of relapse (14 of 28) and 87% of its predictions of non-relapse (33 of 38). Thus, the method of the present invention identified patients with a high (50%) and low (13%) overall relapse rate (p less than 0.002).

Figure 3A:
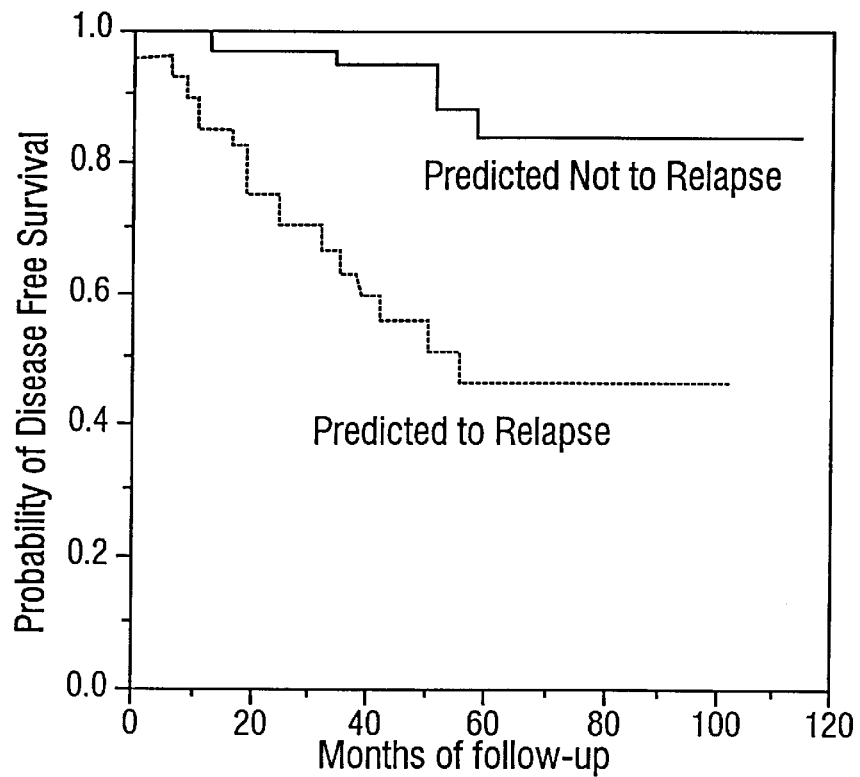
FIGS. 3A and B are graphs of the performance of the present invention to predict relapse rates and mortality of breast cancer patients plotted against follow-up time.
Figure 3B:
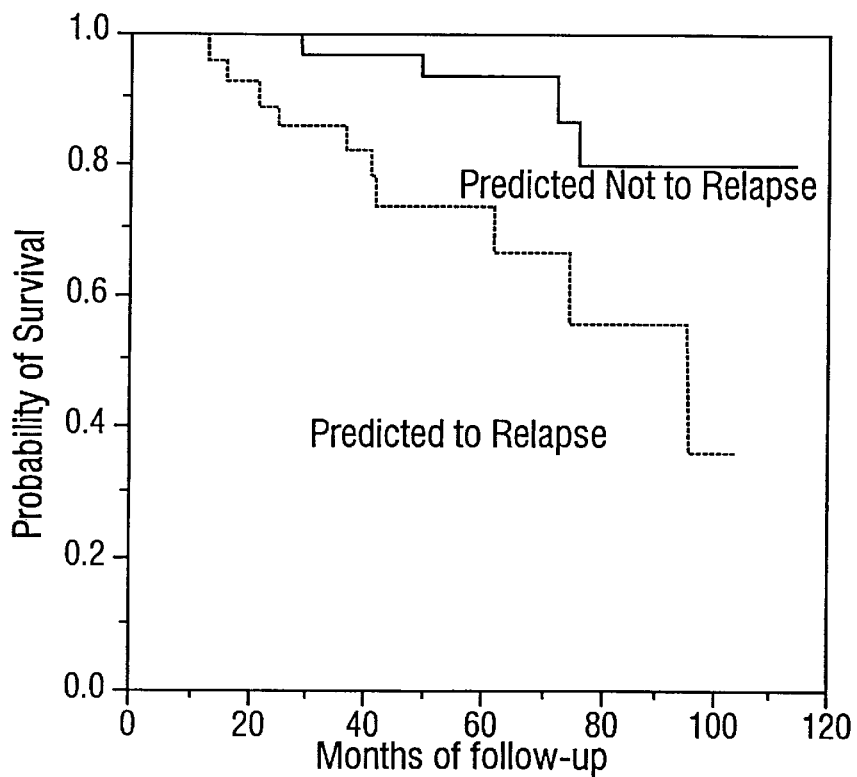

Disease free survival and overall survival curves for the neural network of FIG. 1 with the connection weights shown in Table II, are shown in graphical form in FIGS. 3A and 3B. Projected disease free survival at five years is 86% and 46% in the low and high risk groups, respectively. Projected overall survival at five years was 94% and 67% in the low and high risk groups, respectively. Thus, the predictions produced by the method of the present invention identified a subset of high risk patients that had 3.3 times the relapse rate and 4.4 times the mortality rate of the low risk group. The data presented in Table III shows the disease free and overall survival rates at five years predicted using the neural network method of the present invention, compared with predictions made according to individual prognostic variables using known cut points for the individual variables.

TABLE III

PROGNOSTIC UTILITY OF ANALYTICAL TECHNIQUE
WITH PATIENT DATA FOR PREDICTING RELAPSE
OF OR DEATH DUE TO BREAST CANCER

| Predictor | Favorable | Unfavorable | p |
|---|---|---|---|
| Risk of Relapse at 5 years (%) | | | |
| Neural Network | 16 | 54 | .0004 |
| Progesterone Receptor | 34 | 34 | n.s. |
| Tumor Size | 34 | 34 | n.s. |
| Cathepsin-D | 25 | 52 | .0001 |
| HER-2/neu | 31 | 51 | .11 |
| Overall Risk of Death at 5 Years (%) | | | |
| Neural Network | 6 | 26 | .007 |
| Progesterone Receptor | 13 | 22 | .13 |
| Tumor Size | 16 | 18 | .18 |
| Cathepsin-D | 11 | 33 | .0001 |
| HER-2/neu | 14 | 31 | .02 |

In Table III, percentages of patients in the unfavorable groups (i.e., predicted to relapse) were 42, 49, 64, 32 and 14% of the test set for the neural network method of the present invention, PgR, tumor size, cathepsin-D and HER-2/neu subsets, respectively. For the prognostic variables considered individually, patients were partitioned between favorable and unfavorable subsets as follows: for progesterone receptor with a cut point of >4.9 fm/mg protein, for tumor size with a cut point of >2 cm, for cathepsin-D with a cut point of 75 expression units, and for HER-2/neu with a cut point of 100 expression units. Table III indicates that the method of the present invention is superior to any single prognostic variable for prediction of disease free survival (which was the criteria used to train the network), and is better than progesterone receptor status, tumor size, or HER-2/neu, and is equivalent to cathepsin-D in predicting overall survival.

It should be emphasized that in predicting the possibility of relapse and mortality rate of breast cancer, prognostic variables other than those presented above could be used. For example, other prognostic variables that may be useful for this purpose include % S-phase, nuclear grade, histologic grade, epidermal growth factor content, insulin like growth factor content, other growth factor receptors, transforming growth factor content, epidermal growth factor content, other growth factor and hormone contents, heat shock protein 27 content, other heat shock proteins, Ki67 content, DNA polymerase content, etc. Still other possible prognostic variables include proposed treatments. For example, for breast cancer, possible treatments usable as prognostic variables include various surgical procedures, radiotherapy, or chemotherapy, and combinations thereof. In general, prognostic variables are chosen for their capability, either alone or in combination with other variables, to assist in the prediction of the particular medical condition under consideration. In addition, the present invention can be applied to predict the possible onset or occurrence of diseases and medical conditions other than breast cancer.

Figure 4:
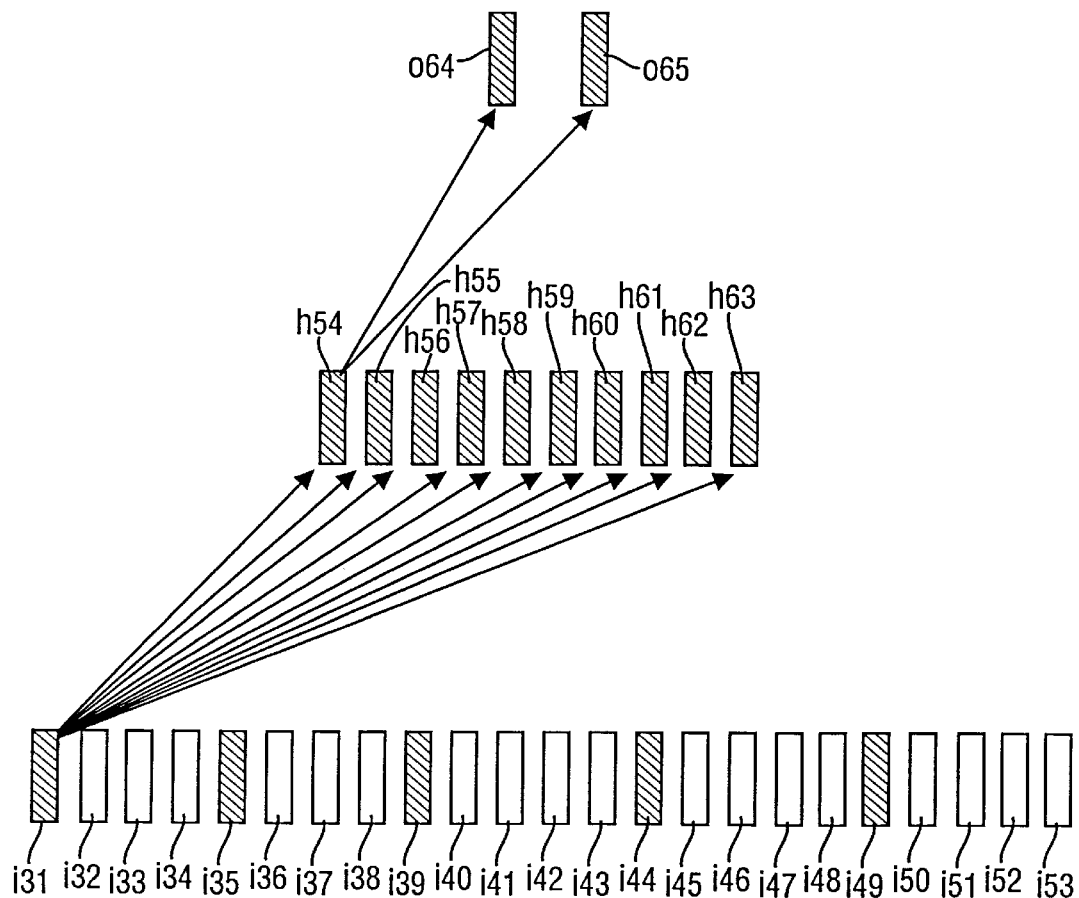
FIG. 4 is a schematic representation of a neural network used to practice the method of the present invention to predict future occurrence of diabetes.

For example, and according to a second exemplary embodiment, the present invention can be applied to evaluate the probability of people developing diabetes mellitus. Referring to FIG. 4, presented is a schematic representation of a neural network used to implement the method of the present invention to predict the occurrence of diabetes. The neural network of FIG. 4, similar to that of FIG. 1, is a three layer back-propagation network, and includes an input layer having 23 input units, i31–i53; a hidden layer having 10 hidden units, h54–h63; and an output layer having two output units, o64 and o65. Once again, for clarity of presentation the weighted connections between only one input unit i31 and the hidden units are shown, and the weighted connections between only one hidden unit h54 and the output units are shown. In fact, the activation states of each input unit i31–i53 are applied through weighted connections to each hidden unit h54–h63, and the activation states of each hidden unit h54–h63 are applied to each output unit, o64 and o65. As before, the activation states of input units i31–i53 are either a one or a zero depending upon the value of the relevant input variable, the activation states of hidden units h54–h63 and output units o64 and o65 are calculated using the weighted activation states of the previous layer in the sigmoidal activation equation, and the value of the connection weights is determined during training of the network using the known back propagation of errors training algorithm. The neural network of FIG. 4 was simulated on a Sun Sparc Station computer using the NeuralWorks Professional II software package available from NeuralWare Inc., of Pittsburgh, Pa.

To train the neural network of FIG. 4, the data was taken from a large survey of non-diabetics in San Antonio, Tex. reported in Haffner, et al. *Diabetes*, 39:283–288, 1990. In this survey, 699 participants were subjected to laboratory tests and physical examination. Then, after eight years, the participants were re-surveyed and their medical records were reviewed to see who had developed diabetes. Approximately 5% of these individuals in the initial survey group developed diabetes.

The 23 input units i31–i53 are divided into five groups, each group dedicated to a particular prognostic variable. In this embodiment, the prognostic variables were patient age in years, fasting glucose level in milligrams per deciliter, two-hour post-prandial glucose level in milligrams per deciliter, fasting serum insulin level in micro International Units per milliliter and body mass index (BMI) in kilograms per meter squared. Input units i31–i34 are dedicated to age, i35–i38 are dedicated to fasting glucose level, i39–i43 are dedicated to two-hour glucose level, i44–i48 are dedicated to fasting insulin level, and i49–i53 are dedicated to BMI. The particular cut points for these input variables are shown in Table IV.

TABLE IV

PARTITIONING OF PROGNOSTIC VARIABLES FOR LATE ONSET (TYPE II) DIABETES MELLITUS BREAK POINTS FOR INPUT UNITS

| Unit | Variable | Range |
| --- | --- | --- |
| i31 | Age | <35 (years) |
| i32 | " | ≥35 and <45 |
| i33 | " | ≥45 and <55 |
| i34 | " | ≥55 |
| i35 | Fasting Glucose | <85 (mg/dl) |
| i36 | " | ≥85 and <90 |
| i37 | " | ≥90 and <96 |
| i38 | " | ≥96 |

TABLE IV-continued

PARTITIONING OF PROGNOSTIC VARIABLES FOR LATE ONSET (TYPE II) DIABETES MELLITUS BREAK POINTS FOR INPUT UNITS

| Unit | Variable | Range |
| --- | --- | --- |
| i39 | 2 Hour Glucose | <90 (mg/dl) |
| i40 | " | ≥90 and <105 |
| i41 | " | ≥105 and <115 |
| i42 | " | ≥115 and <130 |
| i43 | " | ≥130 |
| i44 | Fasting Insulin | unknown |
| i45 | " | <5 ($\mu$I.U./ml) |
| i46 | " | ≥5 and <10 |
| i47 | " | ≥10 and <17 |
| i48 | " | ≥17 |
| i49 | BMI | <23 (kg/m$^2$) |
| i50 | " | ≥23 and <25 |
| i51 | " | ≥25 and <28 |
| i52 | " | ≥28 and <31 |
| i53 | " | ≥31 |

The neural network of FIG. 4 was trained using the known back-propagation of errors algorithm with data from 466 of the 699 participants of the data set being used for training. After 12 training iterations, the connection weights between the various units of FIG. 4 are summarized in Table V.

TABLE V

NEURAL NETWORK CONNECTION WEIGHTS FOR THE PREDICTION OF DIABETES MELLITUS

| TO UNIT NO. | WEIGHT |
| --- | --- |
| WEIGHTS TO OTHER UNITS FROM UNIT NO. i31 | |
| h54 | 1.082 |
| h55 | .1650 |
| h56 | −.3312 |
| h57 | −.3844 |
| h58 | .4208 |
| h59 | .1743 |
| h60 | −.8060 |
| h61 | −.1026 |
| h62 | −.0323 |
| h63 | .5596 |
| WEIGHTS TO OTHER UNITS FROM UNIT NO. i32 | |
| h54 | .4695 |
| h55 | 1.489 |
| h56 | .0136 |
| h57 | .4659 |
| h58 | −.1828 |
| h59 | .5231 |
| h60 | −.3966 |
| h61 | .5845 |
| h62 | .2428 |
| h63 | 1.4569 |
| WEIGHTS TO OTHER UNITS FROM UNIT NO. i33 | |
| h54 | −.9061 |
| h55 | −.3695 |
| h56 | −.2689 |
| h57 | .5337 |
| h58 | −.3899 |
| h59 | .1844 |
| h60 | −.1086 |
| h61 | −1.4047 |
| h62 | −.3271 |
| h63 | −.7362 |
| WEIGHTS TO OTHER UNITS FROM UNIT NO. i34 | |
| h54 | −1.7373 |
| h55 | −.1753 |
| h56 | .8460 |

TABLE V-continued
NEURAL NETWORK CONNECTION WEIGHTS FOR THE PREDICTION OF DIABETES MELLITUS

| TO UNIT NO. | WEIGHT |
| --- | --- |
| h57 | 1.1455 |
| h58 | −.6718 |
| h59 | −.1605 |
| h60 | .4389 |
| h61 | 1.7329 |
| h62 | −2.1717 |
| h63 | .4790 |
| WEIGHTS TO OTHER UNITS FROM UNIT NO. i35 | |
| h54 | −.6124 |
| h55 | 1.1719 |
| h56 | −.2045 |
| h57 | 1.0645 |
| h58 | .4686 |
| h59 | .3892 |
| h60 | .0652 |
| h61 | 1.0425 |
| h62 | −.6701 |
| h63 | −.2960 |
| WEIGHT TO OTHER UNITS FROM UNIT NO. i36 | |
| h54 | −.1561 |
| h55 | .8244 |
| h56 | .5039 |
| h57 | 1.4481 |
| h58 | −.3387 |
| h59 | .3815 |
| h60 | 1.1949 |
| h61 | .2773 |
| h62 | −.9582 |
| h63 | .4250 |
| WEIGHTS TO OTHER UNITS FROM UNIT NO. i37 | |
| h54 | −.1768 |
| h55 | 2.3177 |
| h56 | −.3479 |
| h57 | −.1023 |
| h58 | −.5095 |
| h59 | .5575 |
| h60 | .4405 |
| h61 | −.2545 |
| h62 | −.4639 |
| h63 | .0885 |
| WEIGHTS TO OTHER UNITS FROM UNIT NO. i38 | |
| h54 | .4327 |
| h55 | −1.6347 |
| h56 | −.2518 |
| h57 | −2.1426 |
| h58 | −.6353 |
| h59 | −1.2186 |
| h60 | −1.3275 |
| h61 | −.1426 |
| h62 | 1.1751 |
| h63 | −1.1815 |
| WEIGHTS TO OTHER UNITS FROM UNIT NO. i39 | |
| h54 | −.1423 |
| h55 | .6264 |
| h56 | −.1112 |
| h57 | .2649 |
| h58 | −.5834 |
| h59 | .7100 |
| h60 | −.0177 |
| h61 | .4389 |
| h62 | .5030 |
| h63 | .0028 |
| WEIGHTS TO OTHER UNITS FROM UNIT NO. i40 | |
| h54 | −.5701 |
| h55 | .8938 |
| h56 | −.1702 |
| h57 | .5525 |
| h58 | .5812 |
| h59 | .9000 |
| h60 | .0919 |
| h61 | .1576 |
| h62 | −.7328 |
| h63 | .9492 |
| WEIGHTS TO OTHER UNITS FROM UNIT NO. i41 | |
| h54 | −.8520 |
| h55 | 1.9691 |
| h56 | −.4536 |
| h57 | .3707 |
| h58 | −.3601 |
| h59 | .5104 |
| h60 | .2212 |
| h61 | .5393 |
| h62 | −.9258 |
| h63 | .1085 |
| WEIGHTS TO OTHER UNITS FROM UNIT NO. i42 | |
| h54 | −.3962 |
| h55 | 1.3411 |
| h56 | .6130 |
| h57 | 1.0279 |
| h58 | .2782 |
| h59 | .6524 |
| h60 | −.4333 |
| h61 | .9951 |
| h62 | −.0839 |
| h63 | .6371 |
| WEIGHTS TO OTHER UNITS FROM UNIT NO. i43 | |
| h54 | .2695 |
| h55 | −3.0187 |
| h56 | −1.0331 |
| h57 | −1.8345 |
| h58 | −.1698 |
| h59 | −.9439 |
| h60 | −.7645 |
| h61 | −2.0589 |
| h62 | −.0033 |
| h63 | −1.1946 |
| WEIGHTS TO OTHER UNITS FROM UNIT NO. i44 | |
| h54 | −.6180 |
| h55 | .3870 |
| h56 | −.6375 |
| h57 | .0820 |
| h58 | −.2286 |
| h59 | .6442 |
| h60 | .7407 |
| h61 | .8418 |
| h62 | −.2558 |
| h63 | −.2181 |
| WEIGHTS TO OTHER UNITS FROM UNIT NO. i45 | |
| h54 | −.7152 |
| h55 | .8204 |
| h56 | −.2097 |
| h57 | .3840 |
| h58 | .5409 |
| h59 | −.3277 |
| h60 | .2814 |
| h61 | .7492 |
| h62 | −.3517 |
| h63 | .4750 |
| WEIGHTS TO OTHER UNITS FROM UNIT NO. i46 | |
| h54 | −.5377 |
| h55 | .1972 |
| h56 | .4093 |
| h57 | .4305 |
| h58 | −.2406 |
| h59 | −.0666 |
| h60 | .5703 |

TABLE V-continued

NEURAL NETWORK CONNECTION WEIGHTS FOR THE PREDICTION OF DIABETES MELLITUS

| TO UNIT NO. | WEIGHT |
|---|---|
| h61 | .7781 |
| h62 | −.7824 |
| h63 | −.5787 |
| WEIGHTS TO OTHER UNITS FROM UNIT NO. i47 | |
| h54 | −.1668 |
| h55 | 1.9269 |
| h56 | −.1866 |
| h57 | .7739 |
| h58 | .4460 |
| h59 | .4498 |
| h60 | 1.1424 |
| h61 | 1.1644 |
| h62 | −.1746 |
| h63 | −.1833 |
| WEIGHTS TO OTHER UNITS FROM UNIT NO. i48 | |
| h54 | .2708 |
| h55 | −1.6730 |
| h56 | −.0109 |
| h57 | −.2160 |
| h58 | .1574 |
| h59 | −.2805 |
| h60 | −2.2262 |
| h61 | −2.4391 |
| h62 | .0090 |
| h63 | −1.0066 |
| WEIGHTS TO OTHER UNITS FROM UNIT NO. i49 | |
| h54 | −.1125 |
| h55 | 1.0590 |
| h56 | .3827 |
| h57 | .4043 |
| h58 | −.2512 |
| h59 | −.4271 |
| h60 | .5235 |
| h61 | .5035 |
| h62 | −.6686 |
| h63 | .2838 |
| WEIGHTS TO OTHER UNITS FROM UNIT NO. i50 | |
| h54 | −.6629 |
| h55 | −.1252 |
| h56 | −.1331 |
| h57 | .3879 |
| h58 | −.4655 |
| h59 | .0828 |
| h60 | −1.6439 |
| h61 | −.2371 |
| h62 | .5896 |
| h63 | 1.0295 |
| WEIGHTS TO OTHER UNITS FROM UNIT NO. i51 | |
| h54 | .1780 |
| h55 | 1.5636 |
| h56 | −.4040 |
| h57 | .3184 |
| h58 | −.2704 |
| h59 | .4610 |
| h60 | .7742 |
| h61 | .8869 |
| h62 | .8132 |
| h63 | .2424 |
| WEIGHTS TO OTHER UNITS FROM UNIT NO. i52 | |
| h54 | −.8303 |
| h55 | .6444 |
| h56 | −.1304 |
| h57 | .6764 |
| h58 | .2331 |
| h59 | −.5741 |
| h60 | .4140 |
| h61 | .6549 |
| h62 | −.3536 |
| h63 | −.6422 |
| WEIGHTS TO OTHER UNITS FROM UNIT NO. i53 | |
| h54 | −.3849 |
| h55 | .5199 |
| h56 | .2367 |
| h57 | .8061 |
| h58 | .2046 |
| h59 | −.6376 |
| h60 | .9237 |
| h61 | .7210 |
| h62 | −.7327 |
| h63 | −1.0810 |
| WEIGHTS TO OTHER UNITS FROM UNIT NO. h54 | |
| o64 | .7988 |
| o65 | −.7955 |
| WEIGHTS TO OTHER UNITS FROM UNIT NO. h55 | |
| o64 | −2.5500 |
| o65 | 2.7674 |
| WEIGHTS TO OTHER UNITS FROM UNIT NO. h56 | |
| o64 | −.7810 |
| o65 | .1818 |
| WEIGHTS TO OTHER UNITS FROM UNIT NO. h57 | |
| o64 | −1.3432 |
| o65 | 1.5711 |
| WEIGHTS TO OTHER UNITS FROM UNIT NO. h58 | |
| o64 | −.0919 |
| o65 | −.4624 |
| WEIGHTS TO OTHER UNITS FROM UNIT NO. h59 | |
| o64 | −.9766 |
| o65 | .7307 |
| WEIGHTS TO OTHER UNITS FROM UNIT NO. h60 | |
| o64 | −1.2446 |
| o65 | 1.2364 |
| WEIGHTS TO OTHER UNITS FROM UNIT NO. h61 | |
| o64 | −2.4225 |
| o65 | 2.0069 |
| WEIGHTS TO OTHER UNITS FROM UNIT NO. h62 | |
| o64 | .4785 |
| o65 | .6323 |
| WEIGHTS TO OTHER UNITS FROM UNIT NO. h63 | |
| o64 | −1.1616 |
| o65 | 1.2554 |

After training, data from the remaining 233 patients of the data set was used to evaluate the ability of the network to predict the occurrence of diabetes.

Table VI summarizes the results of the performance of the neural network method of the present invention to predict the occurrence of diabetes compared with the prognostic capabilities of the individual input variables separately. The results indicate that the present invention is capable of identifying a subset of patients with a higher risk of developing diabetes (30%) than has been shown by prior techniques, for example, the technique mentioned in the Haffner article was capable of identifying a group of people with only a 10–20% risk of developing diabetes. The higher accuracy attainable by the present invention has obvious clinical utility as it allows the identification of a subset with a very high risk of developing diabetes for whom special intervention and special further screening would be justified.

TABLE VI

PROGNOSTIC UTILITY OP ANALYTICAL TECHNIQUE WITH PATIENT DATA FOR PREDICTING ONSET OF DIABETES MELLITUS
Risk of Developing Type II Diabetes
After 8 Years of Follow Up (%)

| Predictor | Favorable | Unfavorable | p |
|---|---|---|---|
| Neural Network | 30.0 | 2.8 | <0.001 |
| Age | 7.7 | 4.4 | n.s. |
| Fasting Glucose | 15.8 | 1.2 | <.001 |
| 2 Hour Glucose | 18.5 | 3.0 | <.001 |
| Fasting Insulin Level | 13.2 | 2.0 | <.001 |
| BMI | 7.7 | 3.9 | .009 |

According to yet another embodiment of the present invention, the pattern recognition capabilities of neural network computational systems are exploited to analyze DNA flow cytophotometric measurements for features that correlate with prognosis. At present, several techniques exist to quantitatively estimate a number of nuclear and cellular parameters by processing images of cells obtained by microscopy. Such parameters include nuclear size, nuclear DNA staining, number of nucleoli, and other cellular and nuclear parameters. Data from such studies can be represented in a statistical format such as a histogram of events for a single measured parameter, or in other complex forms with a plurality of parameters for individual cells plotted against each other or plotted against the number of events.

Present analysis of such complex data sets is often quite complex, and can ignore significant attributes of the data that may be valuable in predicting clinical outcome. In accordance with the present invention, a neural network is used to predict prognosis of disease from DNA cytophotometric measurement data.

In particular, according to an exemplary embodiment of the present invention, a neural network is trained to directly predict the risk of relapse of axillary node positive breast cancer patients based on the DNA histograms of their primary tumors. As presented below, the results of the present invention are compared to and used in conjunction with conventional DNA flow cytometric analysis in order to improve the prediction of prognosis in breast cancer.

The analysis was done using the DNA flow histograms of 381 patients who had histologically proven axillary lymph node involvement at the time of a diagnosis of breast cancer, and who had been clinically followed for at least two years or until relapse. All 381 patients had histograms that by use of conventional techniques were interpretable for both ploidy and S-phase.

The preparation of specimens, DNA flow cytometry and the conventional interpretation presented for comparison below was done by Nichols Institute in San Juan, Capistrano, Calif. Clinical follow-up for recording information about relapse was performed by the Nichols Institute research network. Patients were defined as disease free if they had been followed for at least two years, and had not shown any signs of relapse. Patients were defined as having relapsed if they had relapsed within two years of diagnosis.

In order to train and test the neural network of this embodiment of the present invention, the 381 patients were randomly assigned to independent training and testing subsets. To form the combined model of the present invention, the 381 patients were randomly assigned to a 191 patient training set or to a 190 patient testing set. In the diploid and aneuploid models of the present invention, the training and testing subsets were generated from the training and testing sets used for the combined model. For the diploid model, the training set included 98 patients, and the testing set included 84 patients. For the aneuploid model, the training set included 93 patients and the testing set included 106 patients.

To generate the flow histograms for the 381 patients, tumor specimens were prepared by freezing and pulverizing fresh tumor specimens into a coarse powder. The powder was then homogenized into a Tris sucrose buffer, filtered through 210 and 53 micron nylon meshes and debris was removed by a sucrose cushion technique. After centrifugation at 1500 g for 45 minutes, the pellet was resuspended in MEM containing 10% fetal bovine serum. The DNA in the nuclei was then stained with propidium iodide. Nuclei were then pelleted by centrifugation, resuspended in staining buffer, syringed through a 27 gauge needle to break up any clumps, filtered through a 37 micro mesh and injected into a flow cytometer. The flow cytometer used was a Epic V flow cytometer available from Coulter Electronics, of Hialeah, Fla., fitted with a single Inova 90 argon laser available from Coherent Laser Products Division, of Palo Alto, Calif. Laser emission was 400 mW at 488 nm. Approximately 50,000 tumor events were acquired on a single-parameter 256 channel integrated fluorescence histogram.

Using conventional analysis techniques, DNA content or ploidy in a sample was confirmed as diploid if the G0/G1 peak fell between channel 60 to 64 of the 256 channel histogram. The DNA content was defined as aneuploid if two discrete G0/G1 peaks occurred with the aneuploid G0/G1 peak having at least 10% of the 50,000 sample events collected, and having a corresponding G2/M peak. Samples were rejected as uninterpretable if the sample quality was poor (for example, excess cell debris or too few cells), or if the histogram lacked resolution to distinguish two separate peaks. Coefficients of variation of the G0/G1 peak width were required to be less than or equal to 5% to be considered valuable for this conventional study.

In accordance with the present invention, a neural network is used to assess data derived from the 256 channel DNA flow cytometric histograms in order to determine the risk of relapse of breast cancer.

Figure 5:
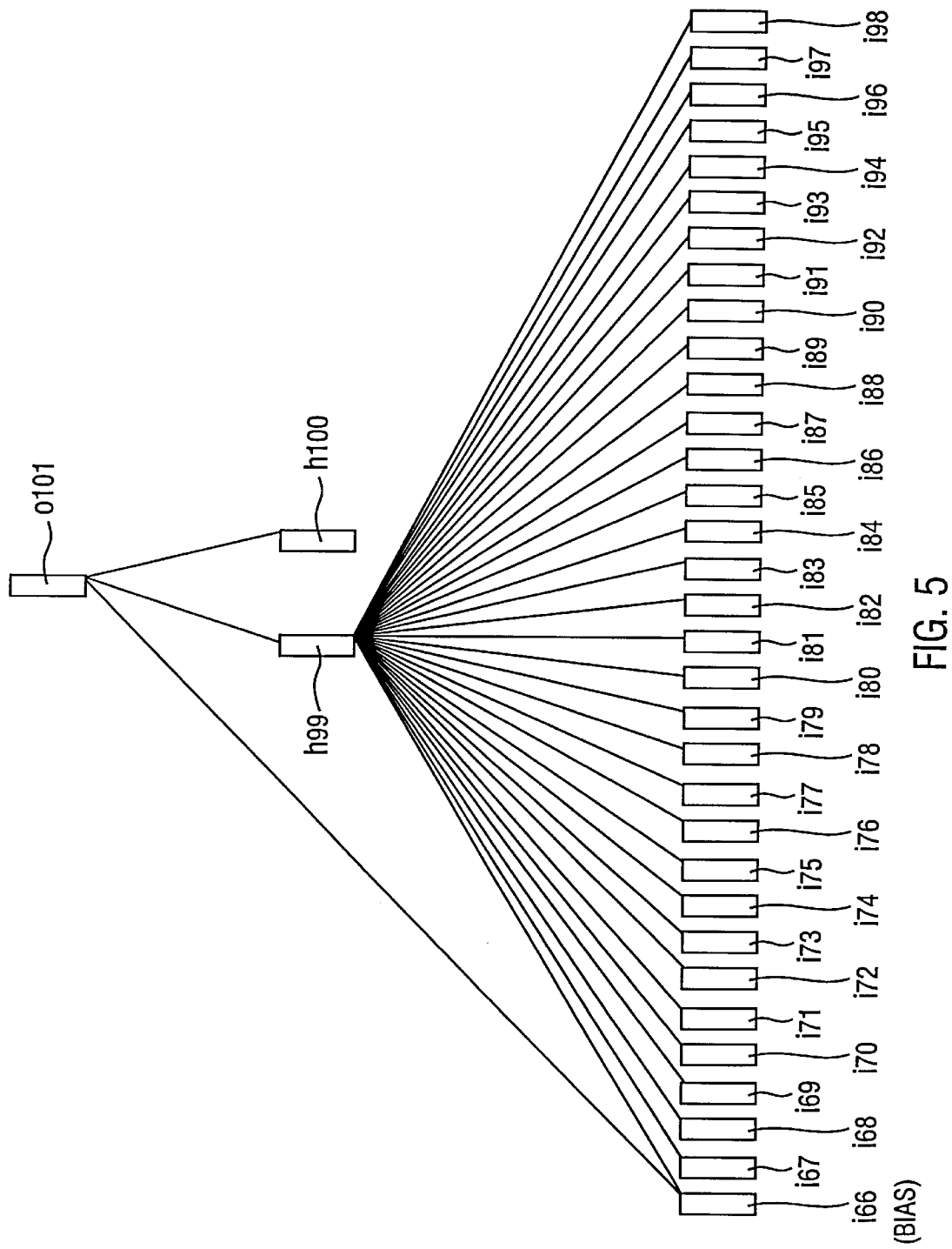
FIG. 5 is a schematic representation of a neural network used to practice another embodiment of the method of the present invention to predict relapse of breast cancer using DNA flow cytometric histograms.

Referring to FIG. 5, the neural network used in this embodiment of the invention is presented. This neural network was simulated using Nworks software available from NeuralWare, Inc. of Pittsburgh, Pa. The network includes 33 input units i66–i98, two hidden layer units, h99 and h100, and one output layer unit, o101. One of the input units, i66, is a bias unit that has a constant input value of 1.0. Bias unit i66 has connection weights to both units of the hidden layer, h99 and h100, and a connection weight to the unit of the output layer, o101. For the sake of clarity, only the connections between input units i66–i98 and one hidden layer unit, h99, are illustrated. However, it is to be understood that each input unit i66–i98 is also connected through weighted connections to hidden layer unit h100.

The transfer functions were linear in the input layer units i66–i98, and were hyperbolic tangent functions (TANH(x)) in hidden layer units h99 and h100 and in output layer unit o101. Use of the hyperbolic tangent function allows scaling of the activation weights to values between −1.0 and 1.0.

The data from the original 256 channel histograms were compressed into 32 channels for application to the neural network of FIG. 5. This compression was done in order to improve the convergence of the network, and was achieved by summing the number of events in 8 consecutive channels of the 256 channel histogram, adding 1.0, taking the log base 10, and dividing by 6. The values in each of the resulting 32 channels in the training examples were further normalized by finding the maximum and minimum values in each channel and by linearly transforming all values in a given channel to lie between −1.0 and 1.0 for presentation to the network.

The cumulative back propagation of errors learning algorithm was used for training the network of FIG. 5 with an epoch of 10 (i.e., correction of connection weight was done after every ten data representations). During training, the 32 compressed histogram channels served as inputs for the 32 input units i67–i98, and the relapse status was presented by the output unit o101 with a 1 representing relapse and a 0 representing non-relapse. After training the network with the training subsets of patients, the network was tested for its ability to generize using a second independent test set of patients. The network was tested after each 250 histogram presentations. The network appeared to reach the best solution within 3,000 data representations, and the performance degraded thereafter. To evaluate the ability of the neural network to discriminate between patients with good and poor prognosis, during testing the value generated by the output unit in response to a histogram was recorded. These output values would ideally be either 1's or 0's corresponding to relapse or non-relapse, but in fact were over a continuous range from 1 to 0. The output values were then ranked from highest to lowest, and the 50% of the patients in the testing set with the highest output values were defined as being in the high risk group, and their relapse rate was calculated. The remaining patients were defined as being in the low risk group, and this group's relapse rate was also calculated.

To test the neural network of the present invention, three different models were used. The first (the combined model), used all of the histogram data divided into a training set and a testing set. The second and third models (diploid and aneuploid models), used only patients from the combined model which were defined by conventional histogram analysis as being diploid or aneuploid. With each of these models, the relapse rate of high and low risk groups was calculated, and the differences in relapse rate were calculated using the chi-square test.

In the combined model, the 381 histograms were randomly assigned to a 191 patient training set or a 190 patient testing set, and the 191 patients in the training set were used to train a series of four neural networks, each of which had a structure identical to that of FIG. 5, with the only difference being the use of four different sets of initial conditions for the connection weights at the beginning of the training session. For each of the four networks, the connection weights in the neural network were initially set before training to random values between −0.2 and 0.2. Table VII presents the connection weights for network no. 1 of the combined model.

TABLE VII

NEURAL NETWORK CONNECTION WEIGHTS
FOR DNA FLOW CYTOMETRIC HISTOGRAMS
(COMBINED MODEL)

| From Unit No. | Weight |
|---|---|
| Weights From Other Units to Unit No. h99 | |
| i66 (Bias) | −0.1176 |
| i67 | −0.0901 |
| i68 | −0.0104 |

TABLE VII-continued

NEURAL NETWORK CONNECTION WEIGHTS
FOR DNA FLOW CYTOMETRIC HISTOGRAMS
(COMBINED MODEL)

| From Unit No. | Weight |
|---|---|
| i69 | +0.0453 |
| i70 | +0.0212 |
| i71 | +0.0469 |
| i72 | −0.0954 |
| i73 | −0.0458 |
| i74 | −0.1189 |
| i75 | −0.0138 |
| i76 | −0.0702 |
| i77 | −0.1570 |
| i78 | −0.1450 |
| i79 | −0.1836 |
| i80 | −0.0503 |
| i81 | −0.0673 |
| i82 | +0.1370 |
| i83 | −0.0756 |
| i84 | −0.0484 |
| i85 | −0.1497 |
| I86 | −0.1163 |
| i87 | −0.1958 |
| i88 | −0.1127 |
| i89 | +0.0718 |
| i90 | +0.0733 |
| i91 | +0.0264 |
| i92 | −0.1320 |
| i93 | −0.0914 |
| i94 | −0.1158 |
| i95 | +0.1360 |
| i96 | +0.0466 |
| i97 | −0.1036 |
| i98 | +0.1672 |
| Weights From Other Units to Unit No. h100 | |
| i66 (Bias) | +0.0799 |
| i67 | −0.0282 |
| i68 | −0.1153 |
| i69 | −0.0797 |
| i70 | −0.0109 |
| i71 | +0.0078 |
| i72 | −0.0473 |
| i73 | −0.1357 |
| i74 | +0.1190 |
| i75 | −0.0484 |
| i76 | −0.0576 |
| i77 | −0.0708 |
| i78 | +0.1290 |
| i79 | +0.0388 |
| i80 | −0.1098 |
| i81 | +0.1266 |
| i82 | +0.0725 |
| i83 | −0.0952 |
| i84 | −0.0587 |
| i85 | +0.1485 |
| i86 | +0.0418 |
| i87 | −0.0675 |
| i88 | +0.1155 |
| i89 | −0.0224 |
| i90 | −0.0047 |
| i91 | −0.0887 |
| i92 | +0.0134 |
| i93 | −0.0199 |
| i94 | +0.0657 |
| i95 | +0.0141 |
| i96 | −0.0535 |
| i97 | +0.0423 |
| i98 | −0.1273 |
| Weights From Other Units to Unit No. o101 | |
| i66 (Bias) | −0.3720 |
| h99 | −0.1787 |
| h100 | +0.0536 |

After training the four combined model networks, the 190 patients assigned to the testing set were used to test the performance of the networks. Table VIII shows the differences in relapse rates in the neural network defined as low and high risk groups.

TABLE VIII

ACTUAL RELAPSE RATES IN THE TESTING SET
(COMBINED MODELS)

| Network | Low Risk | High Risk | p value | Iterations |
|---|---|---|---|---|
| 1 | 12.6% | 27.4% | 0.01 | 500 |
| 2 | 12.6 | 27.4 | 0.01 | 1,000 |
| 3 | 11.6 | 28.4 | 0.003 | 500 |
| 4 | 13.6 | 26.4 | 0.03 | 750 |

Referring to Table VIII, all combined model neural networks achieved a level of discrimination between low and high risk subsets that was statistically significant. Even the weakest network was capable of separating the patients in the testing subsets into a low risk half with a risk of relapse of 13.6% versus a high risk half with a risk of relapse of 26.4%. This discrimination was better than that provided by conventional analysis of ploidy status which separated the patients in the testing set into a diploid set with a relapse rate of 15.5% (43.1% of the patients), and an aneuploid set with a relapse rate of 23.6% (56.9% of the patients). The p value for differences in relapse rate based on ploidy status alone did not reach statistical significance (p>0.10).

To further increase the accuracy of the neural network method of the present invention when analyzing DNA histograms, a combination of conventional techniques and a neural network approach was used. This was accomplished by training a series of four networks, identical in structure to that of FIG. 5, each with different initial conditions, to analyze prognosis after presentation of exclusively diploid DNA histograms (diploid model), and then by training a series of four networks, each with structure identical to that of FIG. 5 with different initial conditions, to analyze prognosis after presentation of exclusively aneuploid DNA histograms as defined by conventional histogram analysis (aneuploid model).

To create the diploid model, training and testing subsets of 98 and 84 patients were selected from the training and testing sets used with the combined model. Table IX presents the connection weights for network no. 1 of the diploid model.

TABLE IX

NEURAL NETWORK CONNECTION WEIGHTS
FOR DNA FLOW CYTOMETRIC HISTOGRAMS
(DIPLOID MODEL)

| From Unit No. | Weight |
|---|---|
| Weights From Other Units to Unit No. h99 | |
| i66 (Bias) | −0.0453 |
| i67 | −0.3006 |
| i68 | −0.3592 |
| i69 | −0.2231 |
| i70 | −0.2721 |
| i71 | −0.2860 |
| i72 | −0.1078 |
| i73 | +0.1925 |
| i74 | −0.3332 |
| i75 | −0.0781 |
| i76 | +0.1240 |
| i77 | +0.1853 |
| i78 | +0.0796 |
| i79 | +0.2817 |

TABLE IX-continued

NEURAL NETWORK CONNECTION WEIGHTS
FOR DNA FLOW CYTOMETRIC HISTOGRAMS
(DIPLOID MODEL)

| From Unit No. | Weight |
|---|---|
| i80 | +0.0874 |
| i81 | −0.2549 |
| i82 | −0.3846 |
| i83 | −0.0600 |
| i84 | +0.3048 |
| i85 | +0.4717 |
| i86 | +0.4189 |
| i87 | +0.2851 |
| i88 | +0.0190 |
| i89 | +0.1962 |
| i90 | +0.0608 |
| i91 | +0.0670 |
| i92 | +0.1140 |
| i93 | +0.0654 |
| i94 | +0.0846 |
| i95 | +0.2185 |
| i96 | −0.0280 |
| i97 | +0.1448 |
| i98 | −0.4853 |
| Weights From Other Units to Unit No. h100 | |
| i66 (Bias) | +0.0179 |
| i67 | +0.2426 |
| i68 | +0.1031 |
| i69 | +0.1885 |
| i70 | +0.2509 |
| i71 | +0.3728 |
| i72 | +0.1957 |
| i73 | −0.1176 |
| i74 | +0.0827 |
| i75 | −0.0517 |
| i76 | −0.3384 |
| i77 | −0.0093 |
| i78 | −0.0712 |
| i79 | −0.1426 |
| i80 | −0.2109 |
| i81 | +0.3254 |
| i82 | +0.2915 |
| i83 | −0.0602 |
| i84 | −0.1110 |
| i85 | −0.4106 |
| i86 | −0.3641 |
| i87 | −0.2332 |
| i88 | −0.0121 |
| i89 | +0.0107 |
| i90 | −0.0194 |
| i91 | −0.0151 |
| i92 | −0.0377 |
| i93 | −0.2963 |
| i94 | +0.0460 |
| i95 | −0.2160 |
| i96 | +0.1115 |
| i97 | −0.0356 |
| i98 | +0.4837 |
| Weights From Other Units to Unit No. o101 | |
| i66 (Bias) | +0.0237 |
| h99 | +0.4966 |
| h100 | −0.4390 |

Table X illustrates that the four neural networks of the diploid model were able quickly and consistently to learn to discriminate between patients with diploid tumors who had a low risk versus a high risk for relapse.

TABLE X

ACTUAL RELAPSE RATES IN THE TESTING SETS
(DIPLOID MODEL)

| Network | Low Risk | High Risk | p value | Iterations |
|---|---|---|---|---|
| 1 | 7.1% | 23.8% | 0.03 | 1,500 |
| 2 | 7.1 | 23.8 | 0.03 | 1,250 |
| 3 | 4.8 | 26.2 | 0.01 | 2,000 |
| 4 | 4.8 | 26.2 | 0.01 | 1,250 |

Referring to Table X, all four networks were able to generate low and high risk subsets with at least a three-fold difference in prognosis (7.1% versus 23.8% relapse, respectively, p=0.03). All four networks of the diploid model were able to do this with statistical significance, and when compared to conventional analysis, which did not reach statistical significance, the neural networks were superior. Conventional analysis for S-phase dichotomized these patients into subsets with 11.9% and 19.0% risk of relapse.

Finally, four neural networks were trained using histograms from patients who had tumor DNA histograms classified as aneuploid by conventional techniques. The training and testing subsets used for these four networks included 93 and 106 patients, respectively, selected from the training and testing sets used in the combined model. Once again, each of the four networks has the structure of FIG. 5, with each having different initial conditions.

Table XI presents the connection weights for network no. 1 of the aneuploid model.

TABLE XI

NEURAL NETWORK CONNECTION WEIGHTS
FOR DNA FLOW CYTOMETRIC HISTOGRAMS
(ANEUPLOID MODEL)

| From Unit No. | Weight |
|---|---|
| Weights From Other Units to Unit No. h99 | |
| i66 (Bias) | +0.1576 |
| i67 | +0.7524 |
| i68 | +0.3201 |
| i69 | +0.0346 |
| i70 | +0.1859 |
| i71 | +0.0828 |
| i72 | −0.1490 |
| i73 | −0.8123 |
| i74 | −0.6118 |
| i75 | +0.2646 |
| i76 | +0.2229 |
| i77 | +0.4630 |
| i78 | −0.1861 |
| i79 | −0.4524 |
| i80 | +0.1341 |
| i81 | −0.1676 |
| i82 | −0.1938 |
| i83 | −0.1521 |
| i84 | −0.3574 |
| i85 | −0.3031 |
| i86 | −0.1846 |
| i87 | −0.2023 |
| i88 | −0.1719 |
| i89 | −0.3219 |
| i90 | −0.3280 |
| i91 | −0.4161 |
| i92 | −0.1316 |
| i93 | +0.4717 |
| i94 | +0.2640 |
| i95 | +0.4035 |
| i96 | −0.1262 |
| i97 | +0.5744 |
| i98 | +0.2289 |

TABLE XI-continued

NEURAL NETWORK CONNECTION WEIGHTS
FOR DNA FLOW CYTOMETRIC HISTOGRAMS
(ANEUPLOID MODEL)

| From Unit No. | Weight |
|---|---|
| Weights From Other Units to Unit No. h100 | |
| i66 (Bias) | +0.0864 |
| i67 | −0.0289 |
| i68 | −0.1330 |
| i69 | −0.0375 |
| i70 | +0.0081 |
| i71 | −0.0259 |
| i72 | +0.0748 |
| i73 | +0.0131 |
| i74 | −0.0284 |
| i75 | −0.1398 |
| i76 | −0.0544 |
| i77 | −0.0025 |
| i78 | −0.0966 |
| i79 | +0.0577 |
| i80 | −0.1182 |
| i81 | +0.0854 |
| i82 | +0.0837 |
| i83 | +0.1469 |
| i84 | +0.0250 |
| i85 | +0.1704 |
| i86 | +0.0461 |
| i87 | +0.1003 |
| i88 | −0.0407 |
| i89 | −0.0659 |
| i90 | +0.0844 |
| i91 | −0.0345 |
| i92 | +0.0006 |
| i93 | −0.1370 |
| i94 | −0.0851 |
| i95 | −0.0653 |
| i96 | +0.1031 |
| i97 | −0.1360 |
| i98 | −0.0752 |
| Weights From Other Units to Unit No. o101 | |
| i66 (Bias) | −0.2751 |
| h99 | −0.5412 |
| h100 | +0.0751 |

Table XII shows the differences in relapse rates that the aneuploid model neural networks defined as low and high risk groups.

TABLE XII

ACTUAL RELAPSE RATES IN THE TESTING SETS
(ANEUPLOID MODELS)

| Network | Low Risk | High Risk | p value | Iterations |
|---|---|---|---|---|
| 1 | 15.1% | 32.1% | 0.04 | 2,250 |
| 2 | 15.1 | 32.1 | 0.04 | 1,500 |
| 3 | 17.0 | 30.1 | 0.11 | 1,750 |
| 4 | 15.1 | 32.1 | 0.04 | 1,750 |

Referring to Table XII, all four neural networks were able to discriminate between histograms with high and low relapse risk. In three out of four cases, this reached statistical significance. In the case of aneuploid tumors, the low risk group had a risk of relapse at two years of 15.1%, while that assigned by conventional S-phase analysis was 13.2%. These two results are not statistically significantly different.

Figure 6:
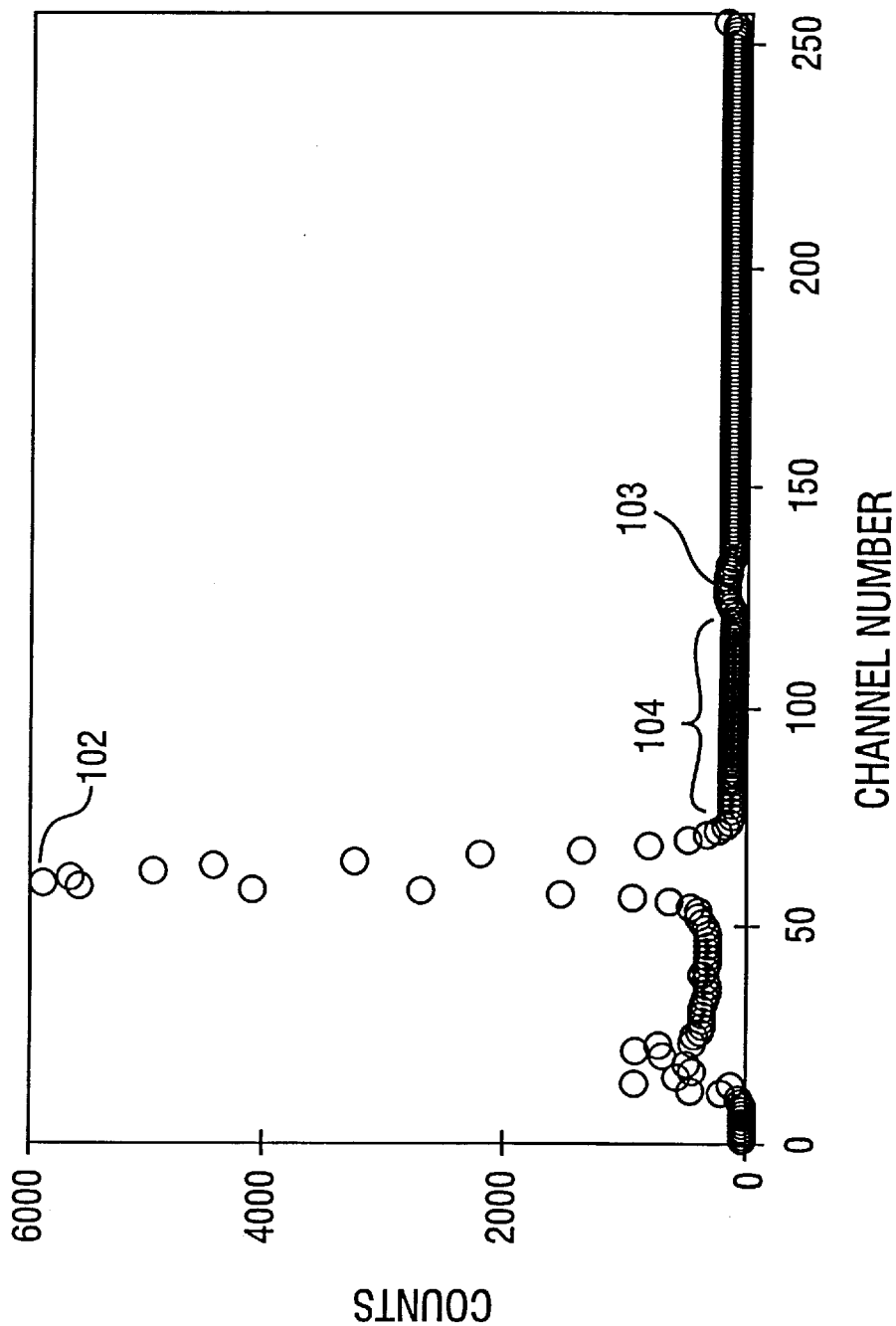
FIG. 6 is a graph of a typical diploid DNA histogram.
Figure 7:
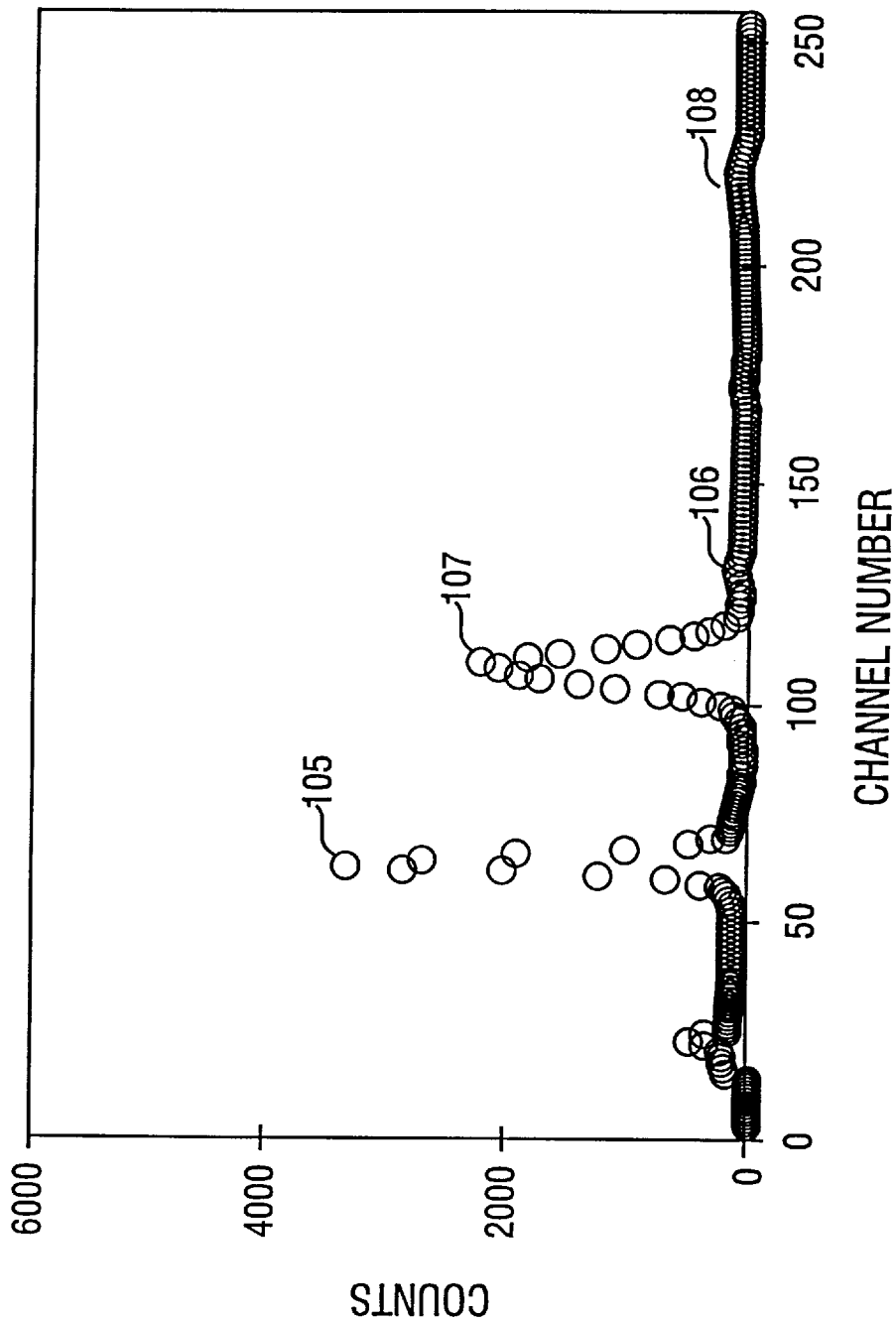
FIG. 7 is a graph of a typical aneuploid DNA histogram.

FIGS. 6 and 7 respectively show typical examples of 256 channel diploid and aneuploid histograms. The diploid histogram of FIG. 6 demonstrates a diploid G0/G1 peak 102, a diploid G2/M peak 103 and a S-phase region 104 between the two. The aneuploid histogram of FIG. 7 also demonstrates a G0/G1 peak 105 and a diploid G2/M peak 106. In addition, the aneuploid DNA histogram of FIG. 7 demonstrates an aneuploid G0/G1 peak 107 and an aneuploid G2/M peak 108.

Figure 8:
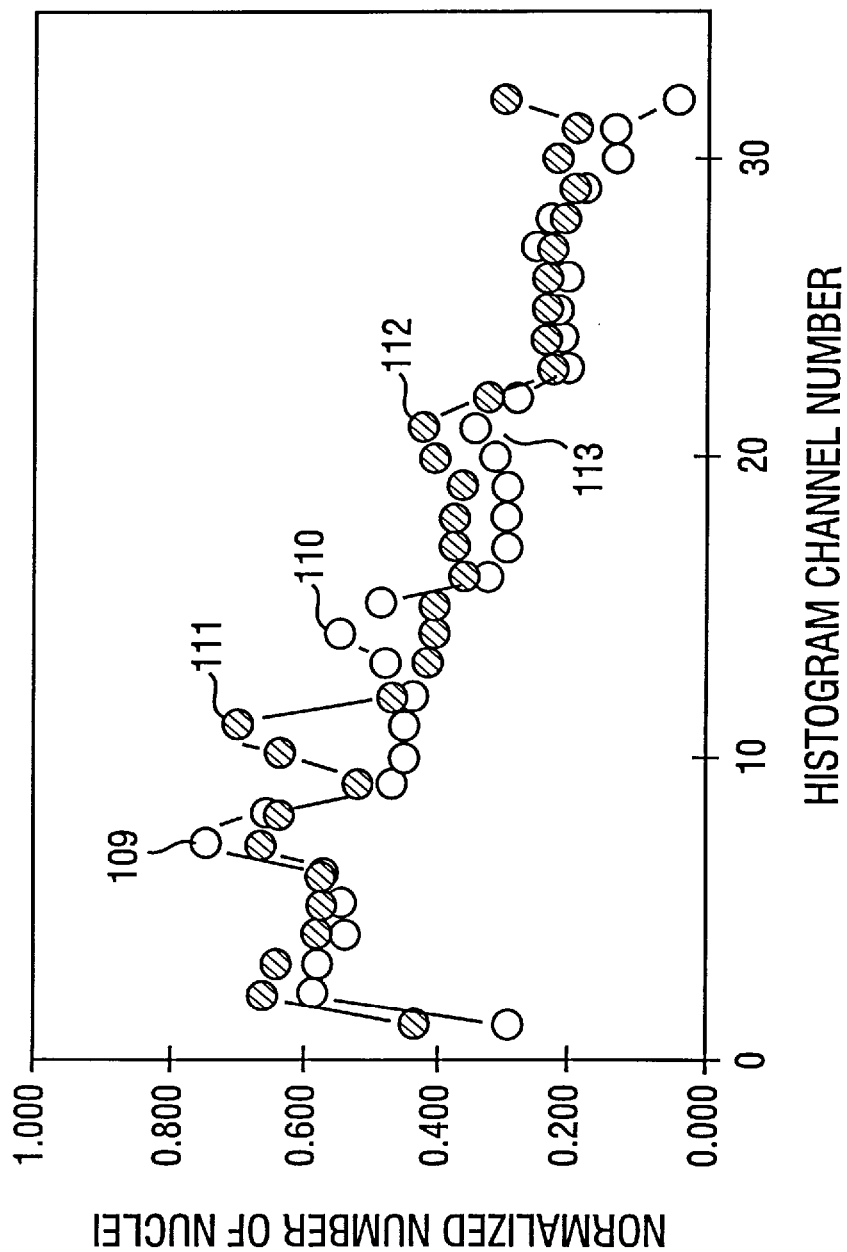
FIG. 8 is a graph of compressed DNA histograms.

FIG. 8 shows typical examples of diploid and aneuploid histograms after compression into 32 channels in accordance with the present invention. The compressed diploid histogram is shown by unfilled circles, and the compressed aneuploid histogram is shown by filled circles. The diploid histogram shows the typical early diploid G0/G1 peak 109 in channels 7 and 8 followed by a G2/M peak 110 in channels 14, 15 and 16. The aneuploid histogram shows in addition to these diploid peaks, an aneuploid G0/G1 peak 111 in channels 10 and 11, and an aneuploid G0/M peak 112 in channels 21 and 22.

Examination of FIG. 8 illustrates the complexity of the histograms. For example, there are a large number of nuclei that do not stain with an intensity represented by any of the channels. This background noise exhibits an exponential decay from low numbered channels to high numbered channels. Discrimination of these background counts from those that are truly S-phase nuclei lying between the G0/G1 peaks and the G2/M peaks is a complex task particularly when multiple G0/G1 peaks exist. There are also frequently peaks that do not correspond to those expected by simple models, such as peak 113 appearing in the diploid histogram in channel 20.

Figure 9:
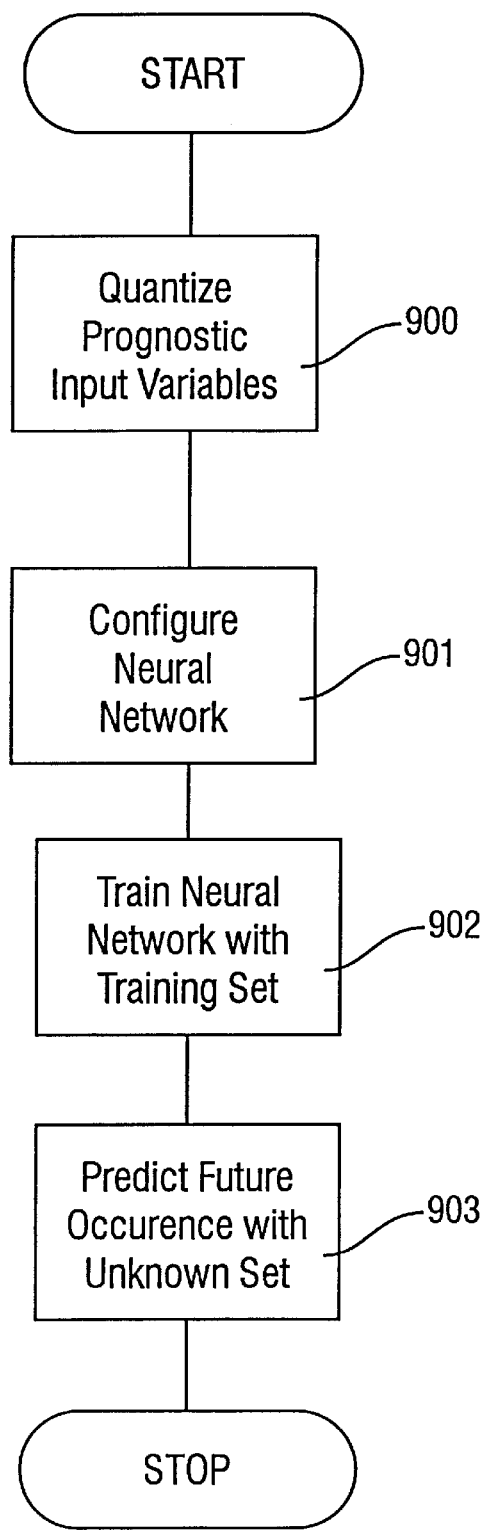
FIG. 9 is a flow chart of the method of the present invention.

Referring now to FIG. 9, presented is a flow chart of the method of the present invention. At the start of the method the prognostic input variables, for example, DNA flow cytometric histograms, are quantized in step 900 then, in step 901 the particular neural network to be used is configured. Then, in step 902, the neural network is trained using first sets of known data, the first sets including the prognostic variables, along with corresponding known occurrence of the medical condition under consideration, for example, breast cancer. Then, in step 903, second sets of data are presented to the trained neural network to predict the future occurrence of the medical condition under consideration. The second sets of data include only values for the prognostic input variables, but do not include the incidence of the medical condition under consideration.

Although the present invention has been described with reference to exemplary embodiments, those of ordinary skill in the art will understand that modifications, additions and deletions can be made to these exemplary embodiments without departing from the spirit and scope of the present invention.

What is claimed is:

1. A method of characterizing DNA cytophotometric data to predict the future occurrence of a target medical condition that is presently clinically occult or non-existing, comprising:

providing a neural network;

data compressing DNA cytophotometric data generated from cells of patients having known occurrence or non-occurrence of said target medical condition to produce a first set of DNA cytophotometric data;

training said neural network using said first set of DNA cytophotometric data; and predicting future occurrence of said target medical condition for at least one additional patient using DNA cytophotometric data obtained from cells of said at least one additional patient and said trained neural network.

2. A method of predicting the relapse of cancer that is presently clinically occult or non-existing, comprising:

providing a neural network;

data compressing a plurality of DNA flow cytometric histograms generated from tumor cells of patients having known cancer relapse rates to produce a first set of histograms;

training said neural network using said first set of DNA flow cytometric histograms;

obtaining at least one DNA flow cytometric histogram from tumor cells of a patient having an unknown cancer relapse rate; and predicting relapse of cancer in said patient having an unknown relapse rate using said at least one DNA flow cytometric histogram and said trained neural network.

3. The method of claim 2, said first set of DNA flow cytometric histograms including diploid histograms and aneuploid histograms.

4. The method of claim 2, said first set of DNA flow cytometric histograms including only diploid histograms.

5. The method of claim 2, said first set of DNA flow cytometric histograms including only aneuploid histograms.

6. The method of claim 2, said cancer comprising breast cancer.

7. A method of predicting the future occurrence of breast cancer that is presently occult or non-existing, comprising:

providing a neural network;

data compressing DNA cytometric data generated from cells of patients having known occurrence of breast cancer to produce a first set of DNA cytometric data;

training said neural network using said first set of DNA cytometric data and first sets of known data, each of said first sets of known data including a predetermined number of prognostic input variables, and corresponding known breast cancer occurrence, said prognostic input variables chosen according to capability to predict occurrence of breast cancer; and predicting future occurrence of breast cancer for a second set of DNA cytometric data and second sets of data using said trained neural network, each of said second sets of data including only said predetermined number of prognostic input variables.

8. The method of claim 7, said neural network comprising a back-propagation class neural network.

9. The method of claim 7, said training step comprising conditioning said first sets of known data using a back-propagation of errors neural network training algorithm.

10. The method of claim 7, further comprising quantizing each of said predetermined number of input variables before said training step.

11. The method of claim 10, said quantizing step comprising:

defining a range for each of said input variables;

dividing each of said ranges into subranges; and determining a subrange within which each of said input variables falls.

12. The method of claim 7, said prognostic input variables comprising proposed treatments for breast cancer.

13. The method of claim 7, said prognostic input variables comprising progesterone receptor status, tumor size, cathepsin D protein level and HER-2/neu protein level.

* * * * *

UNITED STATES PATENT AND TRADEMARK OFFICE
CERTIFICATE OF CORRECTION

PATENT NO. : 5,862,304
DATED : January 19, 1999
INVENTOR(S) : Peter M. Ravdin; William L. McGuire; Gary M. Clark It is certified that error appears in the above-identified patent and that said Letters Patent is hereby corrected as shown below:

On the title page, item 57, line 8, delete "an" and insert --and-- therefor.

Signed and Sealed this

Fifteenth Day of June, 1999

Attest:

Attesting Officer

Q. TODD DICKINSON

Acting Commissioner of Patents and Trademarks

UNITED STATES PATENT AND TRADEMARK OFFICE
CERTIFICATE OF CORRECTION

PATENT NO.    : 5,862,304

DATED         : January 19, 1999

INVENTOR(S)   : Peter M. Ravdin; William L. McGuire; Gary M. Clark

It is certified that error appears in the above-identified patent and that said Letters Patent is hereby corrected as shown below:

In column 1, line 7, insert the following:

--The government owns rights in the present invention pursuant to grant number CA30195 from the National Institutes of Health. The government has certain rights in the invention.--

Signed and Sealed this

Twenty-sixth Day of October, 1999

*Attest:*

Q. TODD DICKINSON

*Attesting Officer*    Acting Commissioner of Patents and Trademarks